United States Patent
Biagini et al.

[11] Patent Number: 6,139,484
[45] Date of Patent: Oct. 31, 2000

[54] BRIDGED CYCLOPENTADIENYL DERIVATIVES AND PROCESS FOR THEIR PREPARATION

[75] Inventors: Paolo Biagini, Trecate; Gabriele Lugli, S. Donato Mil.se; Roberto Santi; Giampiero Borsotti, both of Novara; Viviano Banzi, Vigarano Mainarda, all of Italy

[73] Assignee: Enichem S.p.A., S. Donato Milanese, Italy

[21] Appl. No.: 08/729,302

[22] Filed: Oct. 10, 1996

[30] Foreign Application Priority Data

Nov. 7, 1995 [IT] Italy .................. MI95A2284

[51] Int. Cl.$^7$ ...................... C07F 7/08
[52] U.S. Cl. .............. 572/453; 556/465; 556/489; 585/21; 585/22; 585/27
[58] Field of Search ............... 585/21, 22, 27; 556/453, 489, 465

[56] References Cited

U.S. PATENT DOCUMENTS

| | | |
|---|---|---|
| 5,486,585 | 1/1996 | Murata et al. . |
| 5,541,351 | 7/1996 | Patsidis et al. ............ 556/87 |
| 5,565,592 | 10/1996 | Patsidis et al. . |

FOREIGN PATENT DOCUMENTS

| | | |
|---|---|---|
| 0 628 566 | 12/1994 | European Pat. Off. . |
| WO 95/06071 | 3/1995 | WIPO . |

OTHER PUBLICATIONS

H. Buchholz, et al., Synlett, vol. 1, Jan. 1991, pp 20–22, "Cyclopentadiene Anellated [2.2] Paracyclophanes: Novel Ligands Toward Multilayered Metal Complexes".

C. Mink, et al., Tetrahedron Letters, vol. 35, No. 24, Jun. 14, 1994, pp 4087–4090, "Synthesis and Reactions of Tricyclo [9.3.0.0$^{4,8}$] Tetradeca–4,7,11,14–Tetraene".

*Primary Examiner*—Paul F. Shaver
*Attorney, Agent, or Firm*—Oblon, Spivak, McClelland, Maier & Neustadt, P.C.

[57] ABSTRACT

Bridged cyclopentadienyl derivatives having general formula (I)

$$A—X—B \quad (I)$$

wherein:

1) A is a monofunctional hydrocarbyl radical having general formula (II)

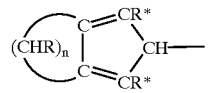

(II)

2) —X— is the bridge between A and B and consists of a bifunctional radical selected from an alkylene group, a silanylene group, an alkyl substituted silaalkylene group, a siloxasilanylene group;

3) B is a monofunctional hydrocarbyl radical selected from:
   e) any of the A radicals defined above,
   f) a cyclopentadienyl radical.

20 Claims, No Drawings

BRIDGED CYCLOPENTADIENYL DERIVATIVES AND PROCESS FOR THEIR PREPARATION

The present invention relates to new bridged compounds of the cyclopentadienyl type and the process for their preparation.

It is known that the most useful soluble catalysts for the homo- and copolymerization of alpha-olefins consist of complexes of zirconium or titanium having ligands of the bis-indenyl, bis-fluorenyl type, or mixed, such as fluorenyl cyclopentadienyl ligands (P.c. Mohring, N.J. Coville, J. Organomet. Chem. 479, 1, 1994).

The ligands can be bridged or non-bridged. The best results, particularly in terms of high molecular weights, are obtained with bridged ligands (see J. C. W. Chien and D. He, Journal of Polymer Science, Part A: Polymer Chemistry, Vol. 29 (1991), page 1585).

Tetrahydroindenyl derivatives are more efficient than the corresponding unsaturated derivatives, particularly in the incorporation of co- and ter-monomers, and are therefore at present among the most widely selected catalysts.

There is the problem, however, that whereas ligands of the indenyl and fluorenyl type are easily available, the corresponding tetrahydroindenyl derivatives are obtained by the direct hydrogenation of the zirconium complex as it is difficult to chemoselectively hydrogenate the starting ligands.

The hydrogenation process of the complex with zirconium has various disadvantages. In fact, as indicated by several experts (see E. Samuel, Bull. Soc. Chim. Fr, 3548, 1966 and S. Collins et al. in J. Organometallic Chem., 342, 21, 1988) there are difficulties in carrying out this hydrogenation due to low yields and/or drastic conditions. In addition, the hydrogenation process of indenyl complexes of zirconium produces two identical ligands of the tetrahydroindenyl type; in fact it is not possible to obtain with this method asymmetrical complexes having one tetrahydroindenyl and one indenyl ligand.

New bridged cyclopentadienyl derivatives have now been found which overcome the disadvantages mentioned above owing to the fact that, as a result of their structure, they do not necessitate the above hydrogenation step.

In accordance with this, the present invention relates to bridged derivatives of cyclopentadienyl having general formula (I)

A—X—B     (I)

wherein

1) A is a monofunctional hydrocarbyl radical having general formula (II)

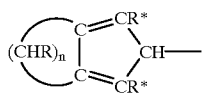

(II)

wherein R and R* are selected from:

H, monofunctional alkyl radicals having from 1 to 3 carbon atoms, monofunctional alkylaryl or aryl radicals, with the proviso that:

the number of R different from H is not more than 2;

at least one R* is H; preferably all the R=H and R* is selected from H and $CH_3$;

2) n is an integer from 2 to 20, and is preferably selected from 3, 4, 5, 6, 10;

3) —X— is the bridge between A and B and consists of a bifunctional radical selected from:

a) a linear, branched or cyclic $C_2$–$C_{20}$ alkylene group;

b) an alkyl or aryl substituted silanylene group having from 1 to 2 silicon atoms;

c) an alkyl substituted silalkylene group;

d) a siloxasilanylene group or —$Si(R_1)_2$—O—$Si(R_2)_2$— tetraalkyl or tetraaryl substituted;

4) B is a monofunctional hydrocarbyl radical selected from:

(e) any of the A radicals defined above;

(f) a cyclopentadienyl radical.

The groups A are monofunctional cyclopentadienyl radicals whose corresponding hydrocarbons, in short hereinafter called AH, are described in copending patent application IT-A-MI 95A 002707. Typical examples of the hydrocarbons AH, having both R*=H, are indicated in Table 1. The names of the above hydrocarbons were obtained using the Autonom program of the Beilstein Institute—Beilstein Information System and the number of carbon atoms is the same as in formula (IIa):

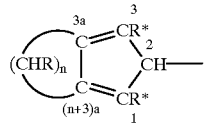

(IIa)

In an embodiment, the hydrocarbons AH, and therefore the corresponding monofunctional hydrocarbyl radicals A, are selected from:

2,4,5,6,7,8-hexahydroazulene (R*=R=H and n=5), 4,5,6,7,8,9-hexahydro-2H-cyclpentacyclooctene (R*=R=H and n=6), 4,5,6,7,8,9,10,11,12,13-decahydro-2H-cyclopentacyclododecene (R*=R=H and n=10), 1-methyl-4,5,6,7,8,9,10,11,12,13-decahydro-2H-cyclopentacyclododecene(R*=$CH_3$, R=H, n=10).

In one embodiment, —X— is a linear, branched or cyclic alkylene radical, having from 2 to 20 carbon atoms. Typical examples of linear —X— are ethylene, propylene, butylene, pentylene, hexylene. Typical examples of branched —X— are isopropylidene ($CH_3$—C—$CH_3$), isobutylidene ($CH_3$—C—$C_2H_5$), 3-pentylene ($C_2H_5$—C—$C_2H_5$), diphenylmethylene ($C_6H_5$—C—$C_6H_5$). Typical examples of cyclic alkylene —X— radical are cyclobutylene, cyclopentylene, cyclohexylene.

In another embodiment —X— is an alkyl or aryl substituted silanylene group having from 1 to 2 silicon atoms, for example dimethylsilanylene, or —$Si(CH_3)_2$—, diethyl silanylene, tetramethyl disilylanylene, or —$Si(CH_3)_2$—Si$(CH_3)_2$, dimethyl diethyl disilanylene, preferably dimethylsilanylene.

In another form of embodiment, the —X— group consists of Silicon-Carbon sequences, i.e. an alkyl substituted silaalkylene group, for example, —$Si(R')_2$—$C(R'')_2$—, wherein R' is a low alkyl and R'' is hydrogen or a low alkyl. Typical examples of silaalkylene groups are:

1-sila-1,1-dimethylethylene,
2-sila-2,2-dimethylpropylene,
1,3-disila-1,1,3,3-tetramethylpropylene.

In another embodiment the X group is a tetraalkyl or tetraaryl substituted siloxasilanylene, i.e. —Si($R_1$)$_2$—O—Si($R_2$)$_2$, wherein $R_1$ and $R_2$, the same or different, can be alkyl or aryl radicals.

In the preferred embodiment —X— is selected from linear or branched alkylene derivatives and dialkylsilanylenes, even more preferably it is selected from ethylene, isopropylidene and dimethylsilanylene.

As far as B is concerned, this is a monofunctional hydrocarbyl radical selected from:

(e) any of the A radicals defined above,
(f) a cyclopentadienyl radical.

When B is equal to any of the A derivatives defined above, the product having general formula (I) will consist of two cyclopentadienyl A derivatives, the same or different, joined to each other in position 2 from the bridge —X—.

We will call these structures A—X—A', wherein A and A', the same or different, both have general formula (II), with the specification that, in the bridged product A—X—A', the double bonds of the cyclopentadienyl ring can be situated in positions 3,3a- and 1,(n+3)a- or in positions 1,2- and 3a,(n+3)a-, where n has the meaning defined above and the numbering of the positions, represented in general formula (IIa) is obtained from the Autonom program mentioned above.

Typical examples of A—X—A' structures, wherein A' is the same or different from A, are indicated in tables 2a, 2b, 2c, 2d.

When B does not belong to the hydrocarbyl radicals having general formula (II), B is a monofunctional cyclopentadienyl radical (f) selected from cyclopentadienyl, indenyl, fluorenyl and the relative alkyl, aryl, trialkylsilyl substituted derivatives; (f) is preferably selected from cyclopentadienyl, indenyl and fluorenyl. For the sake of simplicity we shall call these compounds A—X—C.

It should be noted that, as specified above for the A—X—A' products, in the bridged product A—X—C, the double bonds of the cyclopentadienyl ring of the hydrocarbyl radical A can be situated in positions 3,3a- and 1,(n+3)a- or 1,2- and 3a,(n+3)a- where n has the meaning defined above and the numbering of the positions, represented in general formula IIa, is obtained from the Autonom program mentioned above. We shall call the hydrocarbons corresponding to the monofunctional cyclopentadienyl radicals (f) FH.

The joining point to the bridge —X— of the above cyclopentadienyl derivatives (f) is that which is usually obtained in the known art. For example, indene will be linked to the bridge —X— in position 1 and fluorene in the only non-condensed position of the 5-term cycle.

Tables 3a–3d provide examples of structures of the type A—X—C, wherein C is any of the monofunctional cyclopentadienyl radicals (f).

A further object of the present invention relates to a process for the preparation of the compounds having general formula (I) wherein —X— is selected from branched or cyclic alkylene derivatives and from dialkyl substituted silanylenes.

The above compounds are prepared starting from the hydrocarbons A—H as defined above (i.e. from hydrocarbons corresponding to the radicals A having general formula IIa) and with a process which varies according to the structure of —X—.

When —X— is a difunctional derivative of the type $R_3$—C—$R_4$ wherein $R_3$ and $R_4$ are selected from monofunctional $C_1$–$C_5$ alkyl radicals, phenyl, or $R_3$ and $R_4$ jointly form a $C_4$–$C_5$ alkylene radical, the reaction takes place in two steps.

In accordance with this the present invention relates to a process for the preparation of the compounds having general formula A—X—B, wherein A and B have the meaning defined above and —X— is a radical of the type $R_3$—C—$R_4$, wherein $R_3$ and $R_4$ have the above meaning, which involves the following steps:

i) Condensation between the compound having the general formula A—H defined above and a ketone having the general formula $R_3$—CO—$R_4$ to give the fulvene compound having general formula (III):

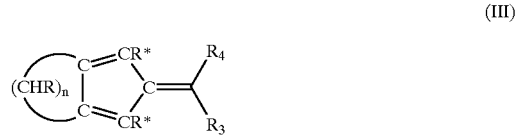

(III)

ii) Addition to the fulvene compound obtained in step (i) of the hydrocarbon BH, the above hydrocarbon BH being selected from any of the hydrocarbons AH and FH defined above.

Step (i) of the above reaction takes place in a basic environment, preferably with an alcoholate of a tertiary alcohol, even more preferably with potassium terbutylate.

Step (ii) of the above process is preferably carried out by preparing the anion of the hydrocarbon BH and subsequently interacting the above anion with the product (III) obtained in step (i).

It should be noted that the process described above enables the preparation of compounds in which —X— forms a bridge between the radical A always in position 2 and the cyclopentadienly radical B in the position specified by the known art.

A further object of the present invention relates to intermediates, of the fulvene type, having general formula (III), wherein n, R, R*, $R_3$ and $R_4$ have the meaning defined above; preferably R=H, R* is selected from H and $CH_3$, $R_3$=$R_4$=$CH_3$ or $C_6H_5$, n is selected from 3,4,5,6,10.

Another object of the present invention relates to a process for obtaining the compounds having general formula A1—X—A1 wherein X is a dialkylsilanylene and the A1 radicals, the same as each other, are selected from the A radicals defined above, which comprises the reaction of the hydrocarbon A1H with a dialkyl dihalogen silane, preferably a dialkyl dichlorosilane, in a molar ratio A1H/dialkyl dihalogen silane of about 2/1.

In a preferred embodiment, the process is carried out by preparing the anion of the hydrocarbon A1H, preferably with an alkyllithium, and interacting the anion thus prepared with the dihalogen silane.

A further object of the present invention relates to a process for obtaining the compounds having general formula A1—X—B wherein:

—X— is a dialkylsilanylene;
A1 is a monofunctional hydrocarbyl radical selected from the A radicals defined above;
B is selected from:
A2, where A2 is any of the A radicals defined above provided it is different from A1,
a cyclopentadienyl radical (f), the above process being carried out in two steps, the first of which (step a) comprising the reaction of the compound A1H with a dialkyl dihalogen silane, preferably a dialkyl dichlorosilane, in a molar ratio A1H/dialkyl dihalogen silane of about 1/1; the second step comprising the reaction of the compound obtained in step (a) with a hydrocarbon BH in an essentially equimolar ratio with respect to the product obtained in step (a).

In the preferred embodiment, the process is carried out by preparing the anion of the hydrocarbon A1H, preferably with alkyllithium, and subsequently reacting, in the first step, the above anion with the dihalogen silane, in a molar ratio essentially consisting of 1/1. In the second step the anion of the hydrocarbon BH is prepared, preferably with an alkyllithium, and the above anion is reacted with the compound obtained in the first step, in a molar ratio of about 1/1.

The following examples provide a better illustration of the present invention.

EXAMPLE 1

Synthesis of bis(2,4,5,6,7,8-hexahydroazulen-2-yl) dimethylsilane 12 ml of a solution of n-butyllithium 2.5 M in hexane are added, at room temperature, to a solution in 100 ml of THF containing 4.1 grams (0.03 moles) of 2,4,5,6,7,8-hexahydroazulene (prepared as described in the copending patent application of the same applicant IT-A-MI 95A 002707). There is an exothermic reaction with the formation of a white solid. The mixture is left under stirring for 2 hours and is then cooled to −70° C. and 1.93 grams (0.015 moles) of dimethyldichlorosilane are added, over a period of about 20 minutes. The temperature is left to rise overnight and a yellow solution is finally obtained.

After evaporation of the solvent, the product is purified on a silica gel column eluting with petroleum ether.

The product obtained is polluted with the starting diene which is removed maintaining the fraction under mechanical vacuum for 24 hours.

2.2 grams of product are obtained (45% yield), which is pure upon NMR and GC analysis.

The $^1$H-NMR spectrum (CDCl$_3$, ppm rel. to TMS) is the following: 6.03 (bs, 4H), 3.07 (bs, 2H) 2.50 (m, 8H), 1.90–1.50 (bs, 12H), −0.2 (s, 6H).

EXAMPLE 2

Synthesis of 2-[1H-Inden-1-yl)-1-methyl-ethyl]-1,4,5,6,7,8-hexahydro-azulene.

A solution is prepared in 10 ml of MeOH and 10 ml of acetone, of 4.5 grams (0.033 moles) of 2,4,5,6,7,8 hexahydroazulene and 0.3 grams of Potassium terbutylate. The above solution is left at reflux temperature for 20 hours, at the end of which a further 2.7 grams of Potassium terbutylate are added. The mixture is maintained at reflux temperature for a further 25 hours, at the end of which the mixture is poured into water and is extracted with ethyl ether.

After neutralisation and anhydrification, the ether extract is evaporated and the residue is purified by elution on a silica gel column with petroleum ether.

3.8 grams of fulvene derivative 2-isopropylidene-2,4,5,6,7,8-hexahydro-azulene are obtained as a yellow solid (66% yield). The $^1$H-NMR spectrum of this compound (CDCl$_3$, ppm rel. TMS) is the following: 6.13 (s, 2H), 2.47 (m, 4H), 2.09 (s, 6H), 1.64 (m, 6H).

An ether solution (100 ml) of Indene (4.0 grams, 0.034 moles) is prepared. 12 ml of a 2.5 M solution in hexane of Butyllithium are added and the mixture is left under stirring for 3 hours.

The fulvene derivative is then added to the above solution, cooled to about −70° C. The temperature is left to rise and the mixture is left under stirring for 48 hours.

The reaction mixture is then hydrolysed in water and is extracted with ethyl ether which, after evaporation, gives a solid which is purified on a silica gel column using petroleum ether as eluant.

4.5 grams of product are obtained (74% yield).

Its $^1$H-NMR spectrum (CDCl$_3$, ppm rel. TMS) is the following: 7.4–7.0 (m, 4H), 6.8 (dd, 1H), 6.45 (dd, 1H), 5.95 (s, 1H), 3.60 (bs, 1H), 3.10 (bs, 2H), 2.40 (m, 6H), 1.23 (s, 3H), 0.94 (s, 3H).

EXAMPLE 3

Synthesis of bis (decahydrocyclopentacyclododecen-2-yl) dimethyl silanes.

22 ml of BuLi 2.5 M in hexane are added to a solution of 11 grams of 4,5,6,7,8,9,10,11,12,13-decahydro-2H-cyclopentacyclododecene, prepared as described in the copending patent application of the same applicant IT-A-MI 95A 002707) in 100 ml of pentane. The mixture is kept under stirring for a night, the solid obtained is filtered and is dried obtaining 9.0 grams of the corresponding Lithium salt.

A solution is prepared in THF (100 ml) of 3.4 grams (0.16 moles) of the above Lithium salt.

1.0 grams (0.008 moles) of dimethyldichlorosilane are added, at −70° C. in about 20 minutes, to this solution in THF. The temperature is then left to rise during a night, obtaining at the end a yellow solution.

After evaporation of the solvent, ethyl ether is added and the mixture is hydrolyzed with dilute hydrochloric acid. The ether extract is washed to neutrality, dried and evaporated. The residue (3.7 grams) is purified on a silica gel column eluting with petroleum ether.

2.2 grams (62% yield) of product are obtained which upon NMR analysis proves to be a mixture of bis(4,5,6,7,8,9,10,11,12,13-decahydro-2H-cyclopentacyclododecen-2-yl) dimethyl silane. $^1$H-NMR (CDCl$_3$, pm rel. TMS): 6.62 (s), 6.39 (bs), 6.21 (bs), 6.12 (bs), 3.23 (m), 2.91 (s), 2.35 (m), 1.88–0.84 (m), 0.08 (bs), −0.21 (bs).

$^{13}$C-NMR (CDCl$_3$, ppm rel. TMS): 153.35, 146.07, 146.02, 141.49, 141.04, 138.44, 132.29, 132.01, 127.09, 125.09, 124.89, 121.46, 61.37, 46.25, 39.49, 32.30, 30.96, 30.76, 28.94, 28.90, 24.30.

EXAMPLE 4

Synthesis of 1,2-bis-(1-methyl-4,5,6,7,8,9,10,11,12,13-decahydro-2-H-cyclopentacyclododecen-2-yl)-dimethyl silane.

28 ml ($70.10^{-3}$ moles ) of BuLi in hexane are added to 15.1 g. ($69.2.10^{-3}$ moles) of 1-methyl-4,5,6,7,8,9,10,11,12,13-decahydro-2H-cyclo pentacyclododecene, prepared according to examples 4 of IT-A-MI 95A 002707, diluted with 100 ml of pentane. The mixture is stirred for a night and then filtered. The solid is recovered and dried: 12 g. of the corresponding Lithium salt are obtained.

To 5.6 g.($25.7.10^{-3}$ moles) of the above Lithium salt, dissolved in 100 ml of anhydrous THF and cooled to −70° C., are added 1.7 g. ($13.2.10^{-3}$ moles) of dichlorosilane; the temperature is then left to rise to 20° C. during a night. After evaporation of the solvent, diethyl ether is added and the reaction mixture is hydrolysed with diluted HCl. The organic phase is washed to neutrality, dried and evaporated. The residue is purified on a silica gel column eluting with petroleum ether.

3.5 g. (55% yield) of 1,2-bis-(1-methyl-4,5,6,7,8,9,10,11, 12,13-decahydro-2-H-cyclopentacyclododecen-2-yl)-dimethyl silane are obtained.

TABLE 1

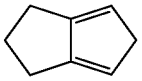

1,2,3,5-tetrahydro-pentalene

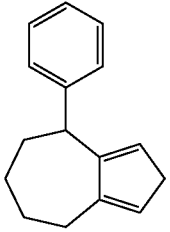

1-methyl-1,2,3,5-tetrahydro-pentalene

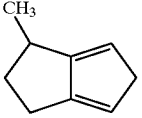

2-methyl-1,2,3,5-tetrahydro-pentalene

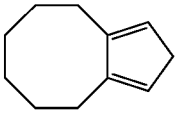

4,5,6,7-tetrahydro-2H-indene

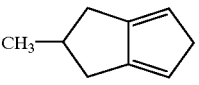

7-methyl-4,5,6,7-tetrahydro-2H-indene

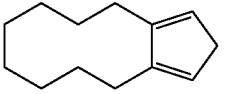

6-methyl-4,5,6,7-tetrahydro-2H-indene

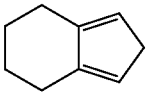

6-ethyl-4,5,6,7-tetrahydro-2H-indene

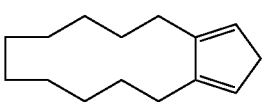

6-phenyl-4,5,6,7-tetrahydro-2H-indene

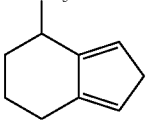

2,4,5,6,7,8-hexahydroazulene

TABLE 1-continued

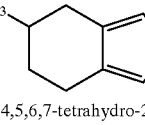

8-phenyl-2,4,5,6,7,8-hexahydro-azulene

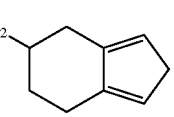

4,5,6,7,8,9-hexahydro-2H-cyclopentacyclooctene

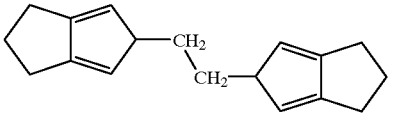

4,5,6,7,8,9,10,11-octahydro-2H-cyclopentacyclodecene

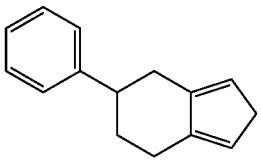

4,5,6,7,8,9,10,11,12,13-decahydro-2H-cyclopentacyclododecene

TABLE 2a

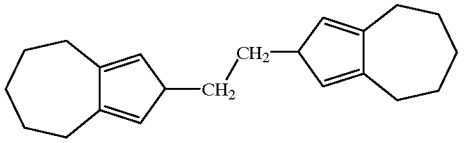

1,2-bis-(2,4,5,6-tetrahydropentalen-2-yl)ethane

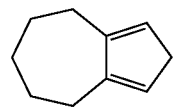

1,2-bis-(2,4,5,6,7,8-hexahydroazulen-2-yl)ethane

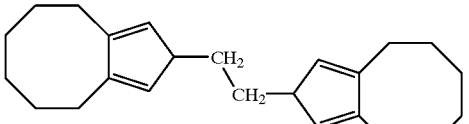

1,2-bis-(4,5,6,7,8,9-hexahydro-2H-cyclopentacyloocten-2-yl)ethane

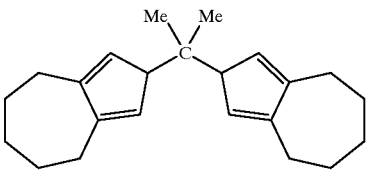

1,1-bis-(2,4,5,6,7,8-hexahydroazulen-2-yl)-1-methyl-ethane

TABLE 2a-continued 1,1-bis-(4,5,6,7,8,9-hexahydro-2H-cyclopentacycloocten-2-yl)-1-methyl-ethane bis-(2,4,5,6-tetrahydropentalen-2-yl)dimethylsilane bis-(2,4,5,6,7,8-hexahydroazulen-2-yl)dimethylsilane 1,2-bis-[1,1,2-trimethyl-(2,4,5,6,7,8-hexahydroazulen-2-yl)]propane TABLE 2b 2-[Dimethyl-(2,4,5,6-tetrahydro-pentalen-2-yl)-silanyl]-2,4,5,6,7,8-hexahydro-azulene 2-[2-(2,4,5,6-Tetrahydro-pentalen-2-yl)-ethyl]-2,4,5,6,7,8-hexahydro-azulene 2-[1-Methyl-1-(2,4,5,6-tetrahydro-pentalen-2-yl)-ethyl]-2,4,5,6,7,8-hexahydro-azulene 2-[Dimethyl-(4,5,6,7-tetrahydro-2H-inden-2-yl)-silanyl]-2,4,5,6,7,8-hexahydro-azulene TABLE 2b-continued 2-[1-Methyl-1-(4,5,6,7-tetrahydro-2H-inden-2-yl)-ethyl]-2,4,5,6,7,8-hexahydro-azulene 2-[Dimethyl-(2,4,5,6-tetrahydro-pentalen-2-yl)silanyl]-4,5,6,7,8,9-hexahydro-2H-cyclopentacyclooctene 2-[1-(2,4,5,6,7,8-Hexahydro-azulen-2-yl)-1-methyl-ethyl]-4,5,6,7,8,9-hexahydro-2H-cyclopentacyclooctene 2-[(2,4,5,6,7,8-Hexahydro-azulen-2-yl)-dimethyl-silanyl]-4,5,6,7,8,9-hexahydro-2H-cyclopentacyclooctene 2-[(2,4,5,6,7,8-Hexahydro-azulene-2-yl)-dimethyl-silanyl]-4,5,6,7,8,9,10,11,12,13-decahydro-2H-cyclopentacy-clododecene 2-[1-(2,4,5,6,7,8-Hexahydro-azulen-2-yl)-1-methyl-ethyl]-4,5,6,7,8,9,10,11,12,13-decahydro-2H-cyclopentacy-clododecene 2-[1-Methyl-1-(2,4,5,6-tetrahydro-pentalen-2-yl)-ethyl]-4,5,6,7,8,9,10,11,12,13-decahydro-2H-cyclopentacy-clododecene TABLE 2c 2-[Dimethyl-(2,4,5,6-tetrahydro-pentalen-2-yl)-silanyl]-4,5,6,7,8,9,10,11,12,13-decahydro-2H-cyclopentacyclododecene TABLE 2c-continued 2-[(4,5,6,7,8-hexahydro-2H-cyclopentacycloocten-2-yl)-dimethyl-silanyl]-4,5,6,7,8,9,10,11,12,13-decahydro-2H-cyclopentacyclododecene 2-[1-(4,5,6,7,8,9-hexahydro-2H-cyclopentacycloocten-2-yl)-1-methyl-ethyl]-4,5,6,7,8,9,10,11,12,13-decahydro-2H-cyclopentacyclododecene 2-[1-(4,5,6,7,8,9-hexahydro-2H-cyclopentacycloocten-2-yl)-1-phenyl-ethyl]-4,5,6,7,8,9,10,11,12,13-decahydro-2H-cyclopentacyclododecene 2-[1-Methyl-1-(2,4,5,6-tetrahydro-pentaten-2-yl)-ethyl]-4,5,6,7,8,9-hexahydro-2H-cyclopentacyclooctene 2-[(4,5,6,7,8,9-hexahydro-2H-cyclopentacycloocten-2-yl)-diphenyl-methyl]-4,5,6,7,8,9,10,11,12,13-decahydro-2H-cyclopentacyclododecene 2-[2-(2,4,5,6,7,8-hexahydro-azulen-2-yl)-ethyl]-4,5,6,7,8,9-hexahydro-2H-cyclopentacyclooctene 2-[2-(4,5,6,7,8,9-hexahydro-2H-cyclopentacycloocten-2-yl)-ethyl]-4,5,6,7,8,9,10,11,12,13-decahydro-2H-cyclopentacyclododecene 2-[2-(2,4,5,6-tetrahydro-pentalen-2-yl)-ethyl]-4,5,6,7,8,9-hexahydro-2H-cyclopentacyclooctene TABLE 2d bis-(1-methyl-2,4,5,6,7,8-exahydroazulen-2-yl)dimethylsilane bis-(1-methyl-4,5,6,7,8,9-exahydro-2H-cyclopentacycloocten-2-yl)dimethylsilane 1,1-bis-(1-methyl-2,4,5,6,7,8-exahydroazulen-2-yl)-1-methyl-ethane 1,1-bis-(1-methyl-4,5,6,7,8,9-hexahydro-2H-cyclopentacycloocten-2-yl)-1-methyl-ethane 1,2-bis-(1-methyl-2,4,5,6,7,8-exahydroazulen-2-yl)-tetramethyldisilane bis-(1-methyl-4,5,6,7,8,9,10,11,12,13-decahydro-2H-cyclopentacyclododecen-2-yl)-dimethylsilane TABLE 3a 2-(1-Cyclopenta-2,4-dienyl-1-methyl-ethyl)-2,4,5,6,7,8-hexahydro-azulene

TABLE 3a-continued 2-(Cyclopenta-2,4-dienyl-dimethyl-silanyl)-2,4,5,6,7,8-hexahydro-azulene 2-(2-Cyclopenta-2,4-dienyl-ethyl)-2,4,5,6,7,8,-hexahydro-azulene 2-(2-Cylcopenta-2,4-dienyl-1,1,2-trimethyl-propyl)2,4,5,6,7,8-hexahydro-azulene 2-[Dimethyl-(3-methyl-cyclopenta-2,4-dienyl)-silanyl]-2,4,5,6,7,8-hexahydro-azulene 2-[1-Methyl-1-(3-methyl-cyclopenta-2,4-dienyl)-ethyl]-2,4,5,6,7,8,hexahydro-azulene 2-[1-(3-ter-Butyl-cyclopenta-2,4-dienyl)-1-methyl-ethyl]-2,4,5,6,7,8-hexahydro-azulene 2-[1-(1-Methyl-1-(3-trimethylsilanyl-cyclopenta-2,4-dienyl)-ethyl]-2,4,5,6,7,8-hexahydro-azulene

TABLE 3b

2-[dimethyl-(3-trimethlysilanyl-cyclopenta-2,4-dienyl)-silanyl]-2,4,5,6,7,8-hexahydro-azulene 2-[1-methyl-1-(2,3,4,5-tetramethyl-cyclopenta-2,4-dienyl)-ethyl]-2,4,5,6,7,8-hexahydro-azulene 2-[Dimethyl-(2,3,4,5-tetramethyl-cyclopenta-2,4-dienyl)-silanyl]-2,4,5,6,7,8-hexahydro-azulene 2-[2-(2,3,4,5-Tetramethyl-cyclopenta-2,4-dienyl)-ethyl]-2,4,5,6,7,8-hexahydro-azulene 2-[1,1,2-Trimethyl-2-(2,3,4,5-Tetramethyl-cyclopenta-2,4-dienyl)-propyl]-2,4,5,6,7,8-hexahydro-azulene 2-[1-(1H-Inden-1-yl)-1-methyl-ethyl]-1,4,5,6,7,8-hexahydro-azulene

TABLE 3b-continued

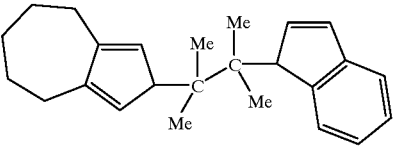

2-[2-(1H-Inden-1-yl)-1,1,2-trimethyl-propyl]-
2,4,5,6,7,8-hexahydro-azulene

TABLE 3c

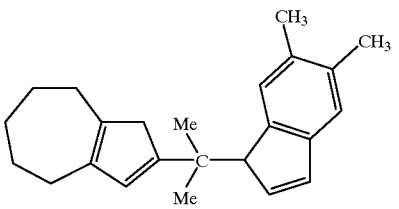

2-[2-(1H-Inden-1-yl)-ethyl]-2,4,5,6,7,8-hexahydro-azulene

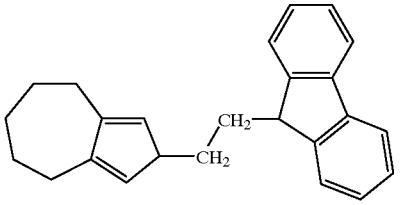

2-[1-Methyl-1-(4-methyl-1H-inden-1-yl)-ethyl]-
1,4,5,6,7,8-hexahydro-azulene

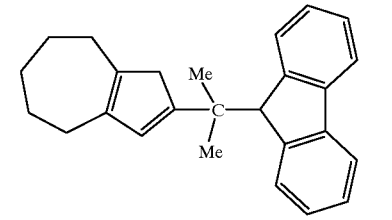

2-[(4,7-Dimethyl-1H-inden-1-yl)-dimethyl-silanyl]-
2,4,5,6,7,8-hexahydro-azulene

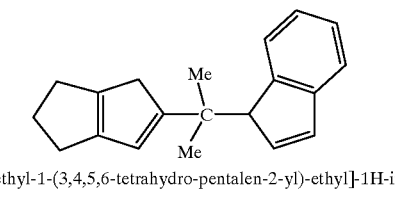

2-[1-(4,7-Dimethyl-1H-inden-1-yl)-1-methyl-ethyl]-
1,4,5,6,7,8-hexahydro-azulene

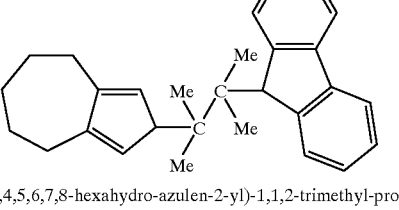

2-[(5,6-Dimethyl-1H-inden-1-yl)-dimethyl-silanyl]-
2,4,5,6,7,8-hexahydro-azulene

TABLE 3c-continued

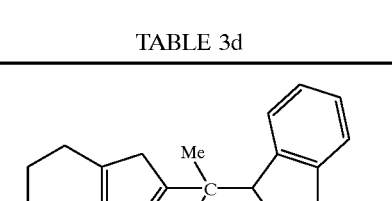

2-[1-(5,6-Dimethyl-1H-inden-1-yl)-1-methyl-ethyl]-
1,4,5,6,7,8-hexahydro-azulene

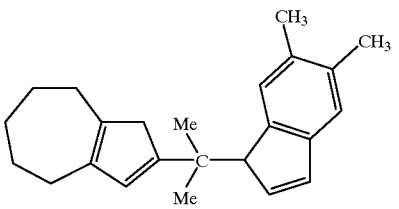

9-[2-(2,4,5,6,7,8-hexahydro-azulen-2-yl)-ethyl]-9H-fluorene

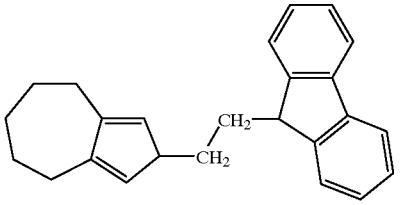

9-[1-(3,4,5,6,7,8-hexahydro-azulen-2-yl)-1-methyl-ethyl]-9H-fluorene

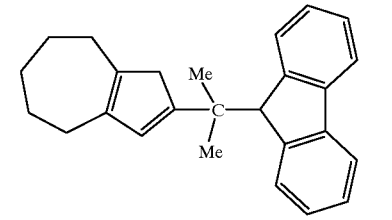

1-[1-Methyl-1-(3,4,5,6-tetrahydro-pentalen-2-yl)-ethyl]-1H-indene

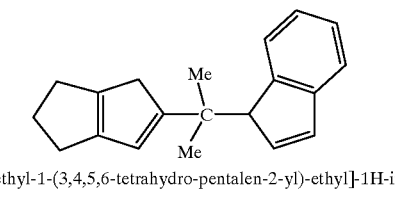

9-[2-(2,4,5,6,7,8-hexahydro-azulen-2-yl)-1,1,2-trimethyl-proply]-
9H-fluorene

TABLE 3d

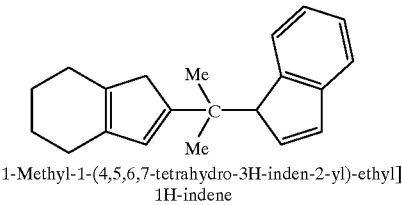

1-[1-Methyl-1-(4,5,6,7-tetrahydro-3H-inden-2-yl)-ethyl]-
1H-indene

TABLE 3d-continued

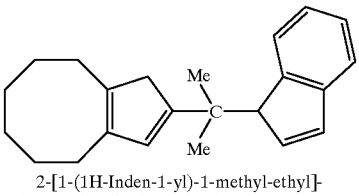

2-[1-(1H-Inden-1-yl)-1-methyl-ethyl]-
4,5,6,7,8,9-hexahydro-1H-cyclopentacyclooctene

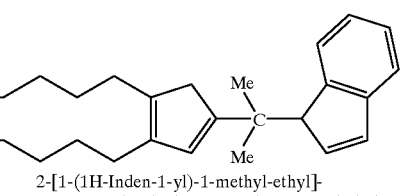

2-[1-(1H-Inden-1-yl)-1-methyl-ethyl]-
4,5,6,7,8,9,10,11,12,13-decahydro-1H-cyclopentacyclododecene

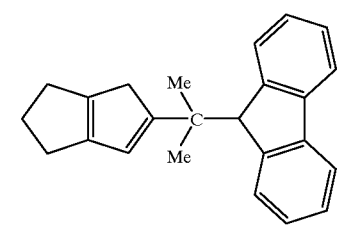

9-[1-Methyl-1-(3,4,5,6-tetrahydro-pentalen-2-yl)-ethyl]-9H-fluorene

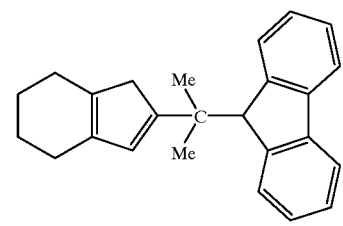

9-[1-Methyl-1-(4,5,6,7-tetrahydro-3H-inden-2-yl)-ethyl]-9H-fluorene

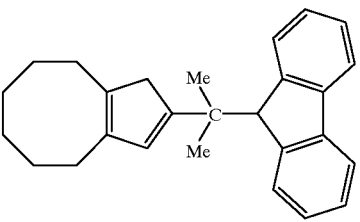

9-[1-(4,5,6,7,8,9-hexahydro-3H-cyclopentacyclooctten-2-yl)-1-methyl-ethyl]-9H-fluorene

What is claimed is:

1. Bridged cyclopentadienyl derivatives having general formula (I)

 (I)

wherein

1) A is a monofunctional hydrocarbyl radical having general formula (II):

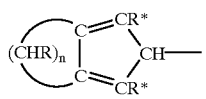 (II)

wherein R and R* are selected from:
- H,
- monofunctional alkyl radicals having from 1 to 3 carbon atoms, or
- monofunctional alkylaryl or aryl radicals, with the proviso that the number of R different from H is not more than 2 and that at least one R* is H;

2) n is an integer from 2 to 20;

3) —X— is the bridge between A and B and consists of a bifunctional radical selected from:
   a) a linear, branched or cyclic $C_2$–$C_{20}$ alkylene group;
   b) an alkyl or aryl substituted silanylene group having from 1 to 2 silicon atoms;
   c) an alkyl substituted silaalkylene group; or
   d) a siloxasilanylene group or —Si$(R_1)_2$—O—Si$(R_2)_2$— tetraalkyl or tetraaryl substituted;

4) B is a monofunctional hydrocarbyl radical selected from:
   (e) any of the A radicals defined above; or
   (f) a cyclopentadienyl radical.

2. The cyclopentadienyl derivatives according to claim 1, wherein all the R=H, R* is selected from H or $CH_3$.

3. The cyclopentadienyl derivatives according to claim 1, wherein n is 3,4,5,6 or 10.

4. The cyclopentadienyl derivatives according to claim 1, wherein R=R*=H and n is 5, 6 or 10.

5. The cyclopentadienyl derivatives according to claim 1, wherein —X— is selected from linear or branched alkylene derivatives or dialkylsilanylenes.

6. The cyclopentadienyl derivatives according to claim 5, wherein —X— is selected from ethylene, isopropylidene or dimethylsilanylene.

7. The cyclopentadienyl derivatives according to claim 1, wherein B is a monofunctional cyclopentadienyl radical (f) selected from cyclopentadienyl, indenyl, fluorenyl or the corresponding alkyl, aryl or, trialkylsilyl substituted derivatives.

8. The cyclopentadienyl derivatives according to claim 7, wherein B is a monofunctional cyclopentadienyl radical (f) selected from cyclopentadienyl, or indenyl or, fluorenyl.

9. A process for the preparation of the compounds having the general formula A—X—B, wherein A and B have the meaning defined in claim 1 and —X— is a radical of the type $R_3$—C—$R_4$, wherein $R_3$ and $R_4$ are selected from monofunctional $C_1$–$C_5$ alkyl radicals, phenyl, or $R_3$ and $R_4$ jointly form a $C_4$–$C_5$ alkylene radical, comprising the following steps:

i) Condensation between the hydrocarbon having the general formula A—H defined above and a ketone having the general formula $R_3$—CO—$R_4$ to give the fulvene compound having general formula (III)

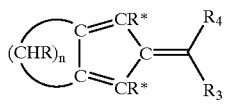

(III)

ii) Addition to the fulvene compound having general formula (III) obtained in step (i), of the hydrocarbon BH, the above hydrocarbon BH being selected from any of the hydrocarbons corresponding to the monofunctional hydrocarbyl radicals (e) and (f) defined in claim 1.

10. The process according to claim 9, characterised in that:

step (i) takes place in a basic environment;

step (ii) is carried out by preparing the anion of the hydrocarbon BH and subsequently interacting the above anion with the fulvene intermediate (III) obtained in step (i).

11. The process according to claim 9, wherein $R^*$ is H and $CH_3$, R=H, $R_3$=$R_4$=$CH_3$ or $C_6H_5$, n is selected from 3,4,5,6 or 10.

12. The process according to claim 11, wherein the ketone having the general formula $R_3$—CO—$R_4$ is acetone and n is selected from 5, 6 or 10.

13. Fulvene derivatives having general formula (III)

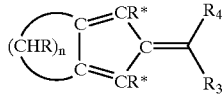

(III)

wherein n, $R^*$, R, $R_3$ and $R_4$ have the meaning as defined in claim 9.

14. Fulvene derivatives according to claim 13, wherein R=H, $R^*$ is selected from H or $CH_3$, $R_3$=—$R_4$=$CH_3$, n is 3,4,5,6 or 10.

15. A process for obtaining the compounds having general formula A1—X—A1 wherein —X— is a dialkylsilanylene and the A1 radicals, the same as each other, are selected from the A radicals defined in claim 1, which comprises the reaction of the hydrocarbon A1H with a dialkyl dihalogen silane, in a molar ratio A1H/dialkyl dihalogen silane of about 2/1.

16. The process according to claim 15, wherein the dialkyldihalogensilane is dialkyldichlorosilane.

17. A process for obtaining the compounds having the general formula A1—X—B wherein:

—X— is a dialkylsilanylene;

A1 is a monofunctional hydrocarbyl radical selected from the A radicals defined in claim 1;

B is selected from:

A2, where A2 is any of the A radicals defined above provided it is different from A1, or a cyclopentadienyl radical (f), the above process being carried out in two steps, the first of which (step a) comprising the reaction of the compound A1H with a dialkyl dihalogen silane, in a molar ratio A1H/dialkyl dihalogen silane of about 1/1; the second step comprising the reaction of the compound obtained in step (a) with a hydrocarbon BH in an essentially equimolar ratio with respect to the product obtained in step (a).

18. The process according to claim 10, wherein step (i) is carried out in the presence of an alcoholate of a tertiary alcohol.

19. The process according to claim 18, wherein said alcoholate of a tertiary alcohol is potassium terbutylate.

20. The process according to claim 17, wherein said dialkyl dihalogen silane is a dialkyl dichlorosilane.

* * * * *